United States Patent [19]
Aukerman et al.

[11] Patent Number: 5,858,977
[45] Date of Patent: Jan. 12, 1999

[54] METHOD OF TREATING DIABETES MELLITUS USING KGF

[75] Inventors: Sharon Lea Aukerman, San Diego; Glenn Francis Pierce, Rancho Santa Fe, both of Calif.

[73] Assignee: Amgen Inc., Thousand Oaks, Calif.

[21] Appl. No.: 817,260

[22] PCT Filed: Oct. 12, 1995

[86] PCT No.: PCT/IB95/00992

§ 371 Date: Apr. 11, 1997

§ 102(e) Date: Apr. 11, 1997

[87] PCT Pub. No.: WO96/11950

PCT Pub. Date: Apr. 25, 1996

Related U.S. Application Data

[63] Continuation-in-part of Ser. No. 323,475, Oct. 13, 1994, abandoned.

[51] Int. Cl.$^6$ .......... C07K 14/475; A61K 38/18
[52] U.S. Cl. .............. 514/12; 514/866; 530/399
[58] Field of Search .................. 514/2, 12, 866; 530/399

[56] References Cited

U.S. PATENT DOCUMENTS 5,626,617  5/1997  Brewitt ........................... 607/2

*Primary Examiner*—John Ulm
*Assistant Examiner*—Christine Saoud
*Attorney, Agent, or Firm*—Thomas D. Zindrick; Richard J. Mazza; Steven M. Odre

[57] ABSTRACT

A method and pharmaceutical compositions are described for the use of keratinocyte growth factor to treat diabetes mellitus in mammals.

11 Claims, 9 Drawing Sheets

FIG.8A human KGF (+ signal sequence)

```
5'CAATCTACAATTCACAGATAGGAAGAGGTCAATGACCTAGGAGTAACAATCAACTCAAGA-
 ---------+---------+---------+---------+---------+---------+ 60

-TTCATTTTCATTATGTTATTCATGAACACCCGGAGCACTACACTATAATGCACAAATGGA-
 ---------+---------+---------+---------+---------+---------+ 120
                                                      M  H  K  W  I

-TACTGACATGGATCCTGCCAACTTTGCTCTACAGATCATGCTTTCACATTATCTGTCTAG-
 ---------+---------+---------+---------+---------+---------+ 180
  L  T  W  I  L  P  T  L  L  Y  R  S  C  F  H  I  I  C  L  V

-TGGGTACTATATCTTTAGCTTGCAATGACATGACTCCAGAGCAAATGGCTACAAATGTGA-
 ---------+---------+---------+---------+---------+---------+ 240
   G  T  I  S  L  A  C  N  D  M  T  P  E  Q  M  A  T  N  V  N

-ACTGTTCCAGCCCTGAGCGACACACAAGAAGTTATGATTACATGGAAGGAGGGGATATAA-
 ---------+---------+---------+---------+---------+---------+ 300
    C  S  S  P  E  R  H  T  R  S  Y  D  Y  M  E  G  G  D  I  R

-GAGTGAGAAGACTCTTCTGTCGAACACAGTGGTACCTGAGGATCGATAAAAGAGGCAAAG-
 ---------+---------+---------+---------+---------+---------+ 360
     V  R  R  L  F  C  R  T  Q  W  Y  L  R  I  D  K  R  G  K  V

-TAAAAGGGACCCAAGAGATGAAGAATAATTACAATATCATGGAAATCAGGACAGTGGCAG-
 ---------+---------+---------+---------+---------+---------+ 420
      K  G  T  Q  E  M  K  N  N  Y  N  I  M  E  I  R  T  V  A  V

-TTGGAATTGTGGCAATCAAAGGGGTGGAAAGTGAATTCTATCTTGCAATGAACAAGGAAG-
 ---------+---------+---------+---------+---------+---------+ 480
       G  I  V  A  I  K  G  V  E  S  E  F  Y  L  A  M  N  K  E  G

-GAAAACTCTATGCAAAGAAAGAATGCAATGAAGATTGTAACTTCAAAGAACTAATTCTGG-
 ---------+---------+---------+---------+---------+---------+ 540
        K  L  Y  A  K  K  E  C  N  E  D  C  N  F  K  E  L  I  L  E

-AAAACCATTACAACACATATGCATCAGCTAAATGGACACACAACGGAGGGGAAATGTTTG-
 ---------+---------+---------+---------+---------+---------+ 600
         N  H  Y  N  T  Y  A  S  A  K  W  T  H  N  G  G  E  M  F  V

-TTGCCTTAAATCAAAAGGGGATTCCTGTAAGAGGAAAAAAAACGAAGAAAGAACAAAAAA-
 ---------+---------+---------+---------+---------+---------+ 660
          A  L  N  Q  K  G  I  P  V  R  G  K  K  T  K  K  E  Q  K  T

-CAGCCCACTTTCTTCCTATGGCAATAACTTAATTGCATATGGTATATAAAGAACCCAGTT
 ---------+---------+---------+---------+---------+---------+ 720
           A  H  F  L  P  M  A  I  T  *
```

FIG.8B

```
-CCAGCAGGGAGATTTCTTTAAGTGGACTGTTTTCTTTCTTCTCAAAATTTTCTTTCCTTT
 --------+---------+---------+---------+---------+---------+ 780

-TATTTTTTAGTAATCAAGAAAGGCTGGAAAAACTACTGAAAAACTGATCAAGCTGGACTT
 --------+---------+---------+---------+---------+---------+ 840

-GTGCATTTATGTTTGTTTTAAG 3'
 --------+---------+-- 862
```

METHOD OF TREATING DIABETES MELLITUS USING KGF

This application is a 35 U.S.C. 371 filing of International Application No. PCT/IB95/00992, filed Oct. 12, 1995, published as WO96/11950 Apr. 25, 1996, which is a continuation-in-part of U.S. application Ser. No. 08/323,475, filed Oct. 13, 1994 (abandoned).

FIELD OF THE INVENTION

The present invention relates to the application of keratinocyte growth factor to treat or prevent the onset of diabetes mellitus.

BACKGROUND OF THE INVENTION

Keratinocyte growth factor (KGF) is a growth factor specific for epithelial cells that was first identified in conditioned medium of a human embryonic lung fibroblast cell line. Rubin et al., *Proc. Natl. Acad. Sci. USA* 86:802–806 (1989). Expression of messenger RNA for KGF has been detected in several stromal fibroblast cell lines derived from epithelial tissues at various stages of development. The transcript for KGF was also evident in RNA extracted from normal adult kidney and organs of the gastrointestinal tract. Finch et al., *Science* 245:752–755 (1989). Evidence that KGF is secreted from fibroblasts in culture and is expressed in vivo in the dermis but not epidermis indicates that KGF may be an important normal paracrine effector of keratinocyte proliferation. Studies have shown that KGF is as potent as EGF in stimulating the proliferation of primary or secondary human keratinocytes in tissue culture. Marchese et al., *J. Cell. Phys.* 144:326–332 (1990).

Ex vivo and in vivo studies in normal adult animals have shown that KGF produces changes in hair follicle morphogenesis, hepatocyte proliferation, and epithelial cell proliferation in the lung, breast, pancreas, stomach, small intestine, and large intestine. Panos et al., *J. Clin. Invest.* 92:969–977 (1993); Ulich et al., *Am. J. Path.* 144:862–868 (1994); Yi et al., *Am. J. Path.* 145:80–85 (1994); and Ulich et al., *J. Clin. Invest.* 93:1298–1306 (1994). The role of KGF in embryonic or neonatal development has not been studied in detail; however, KGF has been documented to be an important mediator of seminal vesicle development in the newborn mouse. Alarid et al., *P.N.A.S.* 91:1074–1078 (1994).

Published PCT patent application WO 90/08771 describes the purification of KGF from the conditioned medium of a human embryonic fibroblast cell line, the partial amino acid sequencing of purified KGF, the cloning of the gene, and the expression of the gene in bacterial cells to yield biologically active recombinant KGF. The aforementioned publication discloses that KGF or KGF-like polypeptides can be used as wound healing agents for burn wounds or to stimulate transplanted corneal tissue. In fact, KGF has been demonstrated to increase re-epithelialization and increased thickness of the epithelium when recombinant KGF was topically applied to wounds surgically induced in the rabbit ear or in porcine skin. Pierce et al., *J. Exp. Med.* 179:831–840 (1994); and Staiano-Coico et al., *J. Exp. Med.* 178:865–878 (1993).

SUMMARY OF THE INVENTION

The discovery has now been made that KGF is useful to treat the medical disorder known as diabetes.

FIG. 1 is a bar graph depicting the effects of KGF in rats following daily subcutaneous administration at a dose of 5 milligrams per kilogram of body weight (mg/kg) over seven days. Streptozotocin (55 mg/kg) was administered once intravenously two days after the initiation of KGF treatment. The KGF-treated group of diabetic rats is shown in the right half of the figure, above the legend "Strep+KGF". Control groups are represented to the left and right of that: treatment over seven days with sodium chloride solution and no diabetes induction ("NaCl"), treatment over seven days with sodium chloride solution before and after streptozotocin-induced diabetes ("Strep"), and treatment over seven days with KGF and no diabetes induction ("KGF"). Non-fasting blood glucose levels in milligrams per deciliter (mg/dl) are shown on the vertical axis, as measured on the fifth day after diabetes induction (i.e., seventh day after KGF or sodium chloride treatment was initiated). There were four rats per group.

FIG. 2 is a bar graph depicting the effect of KGF in the same rat model on other physiological measurements relating to diabetes. Fasting urine glucose levels in mg/dl and fasting urine output in milliliter (ml) excreted in twenty four hours on the seventh day of KGF or sodium chloride treatment are shown on the vertical axis, left half and right half, respectively. Legends ("NaCl", "Strep", "Strep+KGF"and "KGF") have the same meanings as in FIG. 1. There were four rats per group.

FIG. 3 depicts daily non-fasting blood glucose levels in mg/dl in the same rat model of diabetes over an eight day period following diabetes induction. Some animals were treated with a daily subcutaneous dose (3 mg/kg) of KGF beginning one day after disease induction ("Strep+KGF"), while others were pre-and post-treated with sodium chloride solution as a control ("Strep+NaCl"). A non-diabetic group of animals treated with sodium chloride ("NaCl") again served as an additional control. There were six rats per group.

FIG. 4 depicts fasting urine glucose levels in mg/dl for the same rat model over a six day period after diabetes induction, in this case beginning on the second day after the induction of disease. KGF treatment was started one day after the induction of diabetes. Graph symbols designate the same three test groups as in FIG. 3. There were six rats per group.

FIG. 5 shows the urine output, as milliliters per twenty four hour period, from the same test groups as in FIGS. 3 and 4, measured on days 2, 5, 20 and 8 following induction of diabetes. Graph symbols are the same as in FIGS. 3 and 4. There were six rats per group.

FIG. 6 shows the average water intake for each group of rats in the experiment. Rats were given water ad libitum and intake was measured as the volume imbibed in milliliters in twenty four hours. There were six rats per group.

FIGS. 8A and 8B show the nucleotide (SEQ ID NO:1) and amino acid (SEQ ID NO:2) sequences of native KGF (the nucleotides encoding the mature form of native KGF is depicted by bases 201 to 684 of SEQ ID NO:1 and the mature form of KGF is depicted by amino acid residues 32 to 194 of SEQ ID NO:2) with the initial MET in each such sequence being considered residue number "0".

DETAILED DESCRIPTION OF THE INVENTION

Figure 1:
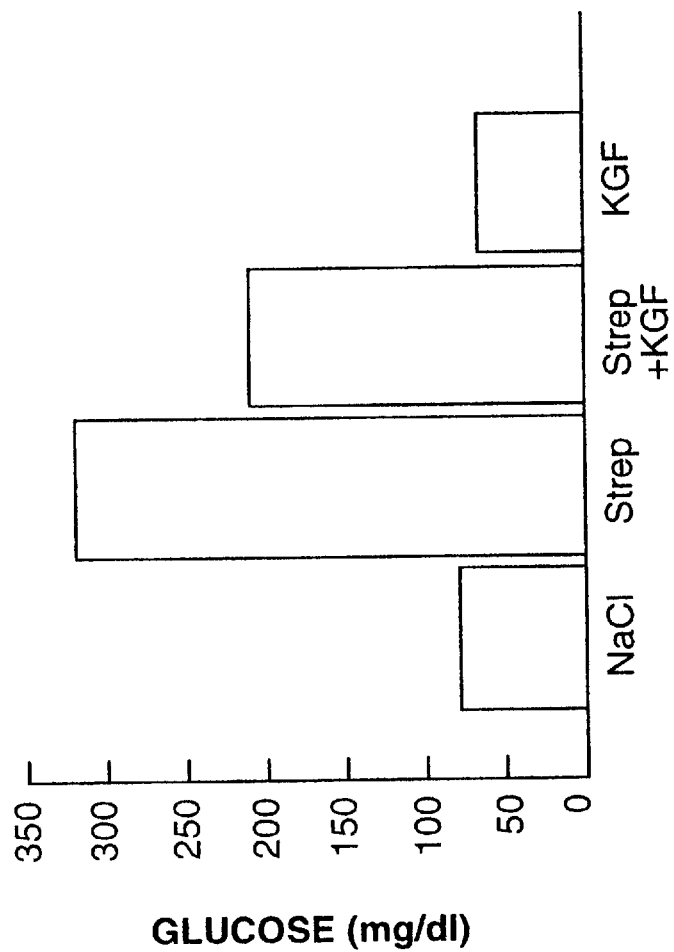

The method of the invention can be practiced using any form of keratinocyte growth factor having some or all of the biological properties of the naturally-occurring polypeptide.

Such forms include those which are isolated and purified from biological fluids, cells and tissues, or which are derived by chemical synthesis or by recombinant means through expression in heterologous host cells that have been transformed with the encoding DNA or RNA. A recombinant process for production of keratinocyte growth factor is described in the previously mentioned WO 90/08771. Other procedures known to those skilled in the art can be adapted for the same purpose.

By way of illustration, the nucleotide sequence coding for KGF protein, or portion thereof, can be inserted into an appropriate expression vector, i.e., a vector which contains the necessary elements for the transcription and translation of the inserted protein coding sequence. The necessary transcriptional and translation signals can also be supplied by the native KGF gene and/or its flanking regions. A variety of host-vector systems may be utilized to express the protein coding sequence. These include but are not limited to mammalian cell systems infected with virus (e.g., vaccinia virus, adenovirus, etc.); insect cell systems infected with virus (e.g., baculovirus) microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of nucleotide fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of a nucleic acid sequence encoding KGF protein or peptide fragment may be regulated by a second nucleic acid sequence so that KGF protein or peptide is expressed in a host transformed with the recombinant DNA molecule. For example, expression of KGF may be controlled by any promoter/enhancer element known in the art. Promoters which may be used to control KGF expression include, but are not limited to, the SV40 early promoter region, the promoter contained in the 3' long terminal repeat of Rous sarcoma virus, the herpes thymidine kinase promoter, the regulatory sequences of the metallothionein gene, prokaryotic expression vectors such as the β-lactamase promoter, or the tac promoter, plant expression vectors comprising the nopaline synthetase promoter region Herrera-Estrella et al., or the cauliflower mosaic virus 35S RNA promoter, and the promoter for the photosynthetic enzyme ribulose biphosphate carboxylase, promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control region, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells Grosschedl et al., mouse mammary tumor virus control region which is active in testicular, breast, lymphoid and mast cells Leder et al., albumin gene control region which is active in liver, alpha fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus.

Expression vectors containing KGF gene inserts can be identified by DNA-DNA hybridization, presence or absence of "marker" gene functions, and expression of inserted sequences, as will be evident and are familiar to those skilled in the art.

Several methods known in the art may be used to propagate the KGF gene. Once a suitable host system and growth conditions are established, recombinant expression vectors can be propagated and prepared in quantity.

In addition, a host cell strain may be chosen which modulates the expression of the inserted sequences, or modifies and processes the gene product in the specific fashion desired. Expression from certain promoters can be elevated in the presence of certain inducers. Thus, expression of the genetically engineered KGF protein may be controlled. Furthermore, different host cells have characteristic and specific mechanisms for the translational and post-translational processing and modification (for example, glycosylation, gamma carboxylation of glutamic acid residues, proteolytic cleavage) of proteins. Appropriate cell lines or host systems can be chosen to ensure the desired modification and processing of the foreign protein expressed.

It should be understood that the terms "keratinocyte growth factor" and "KGF" as employed in this description are intended to include, and to mean interchangeably unless otherwise indicated, native KGF and KGF analog proteins (or "muteins") characterized by a peptide sequence substantially the same as the peptide sequence of native KGF and by retaining some or all of the biological activity of native KGF, particularly non- fibroblast epithelial cell proliferation (e.g., exhibiting at least about 500-fold greater stimulation of BALB/MK keratinocyte cells than that of NIH/3T3 fibroblast cells, and at least about 50-fold greater stimulation of BALB/MK keratinocyte cells than for BS/589 epithelial cells or for CC1208 epithelial cells, as determined by H-thymidine incorporation). By "characterized by a peptide sequence substantially the same as the peptide sequence of native KGF" is meant a peptide sequence which is encoded by a DNA sequence capable of hybridizing of nucleotides 201 to 684 of SEQ ID NO:1, preferably under stringent hybridization conditions.

The determination of a corresponding amino acid position between two amino acid sequences may be determined by aligning the two sequences to maximize matches of residues including shifting the amino and/or carboxyl terminus, introducing gaps as required and/or deleting residues present as inserts in the candidate. Database searches, sequence analysis and manipulations may be performed using one of the well-known and routinely used sequence homology/identity scanning algorithm programs (e.g., Pearson and Lipman (1988), *Proc. Natl. Acad. Sci. U.S.A.*, 85:2444–2448; Altschul et al. (1990), *J. Mol. Biol.*, 215:403–410; Lipman and Pearson (1985), *Science*, 222:1435 or Devereux et al. (1984), *Nuc. Acids Res.*, 12:387–395).

Stringent conditions, in the hybridization context, will be stringent combined conditions of salt, temperature, organic solvents and other parameters typically controlled in hybridization reactions. Exemplary stringent hybridization conditions are hybridization in 4×SSC at 62°–67° C., followed by washing in 0.1×SSC at 62°–67° C. for approximately an hour. Alternatively, exemplary stringent hybridization conditions are hybridization in 45–55% formamide, 4×SSC at 40°–45° C. [See, T. Maniatis et. al., *Molecular Cloning* (A Laboratory Manual); Cold Spring Harbor Laboratory (1982), pages 387 to 389].

Thus, the proteins include allelic variations, or deletion (s), substitution(s) or insertion(s) of amino acids, including fragments, chimeric or hybrid molecules of native KGF. One example of KGF includes proteins having residues corresponding to $Cys^1$ and $Cys^{15}$ of SEQ ID NO:2 replaced or deleted, with the resultant molecule having improved stability as compared with the parent molecule (as taught in commonly owned U.S. Ser. No. 08/487,825, filed on Jul. 7, 1995). Another example of KGF includes charge-change polypeptides wherein one or more of amino acid residues 41–154 of native KGF (preferably residues $Arg^{41}$, $Gln^{43}$, $Lys^{55}$, $Lys^{95}$, $Lys^{128}$, $Asn^{137}$, $Gln^{138}$, $Lys^{139}$, $Arg^{144}$, $Lys^{147}$ $Gln^{152}$, $Lys^{153}$ or $Thr^{154}$) are deleted or substituted with a neutral residue or negatively charged residue selected to effect a protein with a reduced positive charge (as taught in commonly owned U.S. Ser. No. 08/323,337, filed on Oct. 13, 1994). A still further example of KGF includes proteins generated by substituting at least one amino acid having a higher loop-forming potential for at least one amino acid within a loop-forming region of $Asn^{115}$-$His^{116}$-$Tyr^{117}$-$Asn^{118}$-$Thr^{119}$ of native KGF (as taught in commonly owned U.S. Ser. No. 08/323,473, filed on Oct. 13, 1994). A still yet further example includes proteins having one or more amino acid substitutions, deletions or additions within a region of 123–133 (amino acids 154–164 of SEQ ID NO:2) of native KGF; these proteins may have agonistic or antagonistic activity.

Specifically disclosed proteins include the following KGF molecules (referred to by the residue found at that position in the mature protein (minus signal sequence) set forth in SEQ ID NO:2, followed by that amino acid position in parentheses and then either the substituted residue or "–" to designate a deletion): C(1,15)S, ΔN15–ΔN24, ΔN3/C(15)S, ΔN3/C(15)-, ΔN8/C(15)S, ΔN8/C(15)-, C(1,15)S/R(144)E, C(1,15)S/R(144)Q, ΔN23/R(144)Q, C(1,15,40)S, C(1,15, 102)S, C(1,15,102,106)S, ΔN23/N(137)E, ΔN23/K(139)E, ΔN23/K(139)Q, ΔN23/R(144)A, ΔN23/R(144)E, ΔN23/R (144)L, ΔN23/K(147)E, ΔN23/K(147)Q, ΔN23/K(153)E, ΔN23/K(153)Q, ΔN23/Q(152)E/K(153)E; R(144)Q and H(116)G.

For practical application in therapeutic treatment, KGF can be formulated into appropriate pharmaceutical compositions for administration by any conventional means, including but not limited to parenteral delivery, such as subcutaneous, intravenous or intramuscular injection. These standard formulations would most likely include suitable buffer salts, preservatives and stabilizing agents for a liquid formulation or suitable buffer salts, stabilizing agents, preservatives and bulking agents typical for a lyophilized formulation. It is also possible that KGF could be administered in a slow release form, by intradermal, subcutaneous, or intra-abdominal depot. These slow release forms of KGF can be formulated using standard methods within the skill of those knowledgeable in the art. The most practical administration regimens for KGF can be utilized by the patient at home using subcutaneous injection or intradermal delivery, or by the physician using a long-term slow release formulation implanted subcutaneously or in the peritoneal cavity.

The dosing regimen for KGF can be determined empirically by the skilled practitioner. In general, it is anticipated that KGF will be effective in amounts from about 0.001 to about 10 milligrams per kilogram of body weight (of the patient) per day, and preferably from about 0.05 to about 5 mg/kg/day. The therapeutic regimen can include single or repeated injections, or a slow continuously released low dose of KGF, depending on the type and severity of the disease in each patient. The therapeutic course of treatment with KGF must produce enough pancreatic beta cell function in order to normalize blood glucose levels during varying metabolic demands, yet avoid frequent or profound hypoglycemia. The aim is to replenish the islet cell function of patients with diagnosed Type I diabetes to avoid the necessity of constant exogenous insulin requirements. Patients with newly diagnosed Type I diabetes, in whom some islet cell function remains, would be candidates for KGF therapy. KGF could be used to maintain the islet function of such patients so as to ameliorate, delay, or circumvent permanent manifestation of disease. Type I diabetes is believed to be an autoimmune disease and immunosuppressant therapy is used for its treatment. KGF therapy in accordance with this invention can be used in conjunction or combination with immunosuppressants for treatment of the disease, including as an adjunct in the setting of islet cell transplantation. The invention is further illustrated with reference to the following application.

Materials

The test materials used in the following in vivo studies were, as specifically indicated KGF of native (naturally occurring) sequence, a KGF analog in which the cysteine residues at positions 1 and 15 of the native amino acid sequence had been replaced with serine using standard techniques of site directed mutagenesis (i.e., C(1,15)S) and a KGF analog having a deletion of the first 23 amino acids of the N-terminus of native KGF using standard techniques (i.e., ΔN23). All proteins were produced by recombinant expression in E. coli and purified to homogeneity, and they each contained a methionine residue ($Met^{-1}$) at the N-terminus. Each protein was administered as a subcutaneous formulation. Previous experiments demonstrated that these proteins had comparable activities in adult rats when administered systemically. The native sequence KGF and the analogs each had comparable activities in the diabetic and non-diabetic rats used in the following studies.

In Vivo Model of Diabetes

Chemically-induced diabetes mellitus models in various animal species have been classically used to study the disease and its treatment. Streptozotocin induces diabetes in the mouse, rat, hamster, dog, and monkey although studies in rats and mice are utilized most. Junod et al., *Proc. Soc. Exp. Pio. Med.* 126:210–205 (1967); Rerup, *Pharm. Rev.* 22:485–518 (1970); Rossini et al., *P.N.A.S.* 74:2485–2489 (1977); and *Ar'Rajab and Ahren, Pancreas* 8:50–57 (1993). In rats, doses of streptozotocin from 45 to 70 mg/kg as a single intravenous dose induce stable disease. Doses below 45 mg/kg induce a transient disease state which is reversible. Within one day of streptozotocin injection, the hyperglycemic state is induced. Blood insulin levels remain essentially unchanged compared with normal rats; however, the total content of insulin and C-peptide in the pancreas is severely decreased. Rats manifest the classic signs and symptoms of diabetes in humans: increased blood glucose levels (hyperglycemia), glucose in the urine (glucosuria), increased thirst (polydipsia), increased urination (polyuria), increased appetite (hyperphagia).

The studies described in this disclosure were carried out with the streptozotocin-induced diabetes model in Sprague-Dawley rats. Male rats weighing 200–260 grams at study initiation were used. Diabetes was induced by a single intravenous injection of streptozotocin at 50 mg of streptozotocin in sodium citrate buffer per kg of body weight. Non-diabetic control rats received a single intravenous injection of sodium citrate buffer for control purposes. KGF was administered daily as a subcutaneous injection. The KGF dose was 3 or 5 mg/kg/day, depending upon the experiment. In the first experiment, KGF therapy was initiated two days before diabetes, was induced and continued after the induction of diabetes for a total of eight injections.

In the second and third experiments, KGF therapy administered subcutaneously was initiated one day after the induction of diabetes with streptozotocin. In the fourth experiment, a 7 day course of KGF therapy was initiated 7 days after streptozotocin treatment and the animals were then followed for an additional 12 weeks. In all experiments, except for the fourth experiment, blood glucose levels, urine glucose levels and urine volume were used as end points for analysis. Additionally, water intake, urine C-peptide levels, or total pancreatic insulin and C-peptide content were measured in some experiments. In the fourth experiment, the only assessed endpoint was blood glucose.

Because a large fraction of insulin is removed from the circulation by the liver, measurement of peripheral insulin concentrations reflect post-hepatic metabolism events rather than insulin secretion from the pancreas. Therefore, measurements of C-peptide are often made and used as a peripheral marker of insulin secretion. C-peptide is produced from the processing of pro-insulin to insulin. Insulin and C-peptide are secreted from the beta cells in equimolar amounts, and only a small amount of C-peptide is extracted by the liver.

In Vivo Administration of KGF

First Study: Using the diabetes model described, the effectiveness of KGF to treat diabetes was first evaluated using the following four groups of test rats:

1. Control (non-diabetic) rats pre- and post-treated with subcutaneously administered sodium chloride solution, no streptozotocin;
2. Rats made diabetic with intravenously administered 50 mg/kg of streptozotocin, pre- and post-treated with subcutaneously administered sodium chloride solution;
3. Rats made diabetic with intravenously administered 50 mg/kg streptozotocin, pre- and post-treated with subcutaneously administered native KGF; and
4. Control rats treated with subcutaneously administered native KGF, no streptozotocin.

Rats treated in all four groups were administered with either native KGF at a dose of 5 mg/kg per day or an equal volume of sodium chloride solution over a period of seven days. Two days after the commencement of KGF or sodium chloride administration, the rats in groups 2 and 3 were given a single dose of 55 mg/kg of streptozotocin, administered intravenously. This dose is known to cause moderate diabetes in rats. All rats were monitored for non-fasting blood glucose level, body weight, fasting urine glucose level-and urine output. Seven days after administration of streptozotocin to groups 2 and 3 (i.e., nine days after commencement of the study) the rats in all of the groups were fasted overnight, sacrificed, then necropsied. In each case the pancreas was preserved in zinc formalin, embedded, then processed for routine histopathology.

Figure 2:
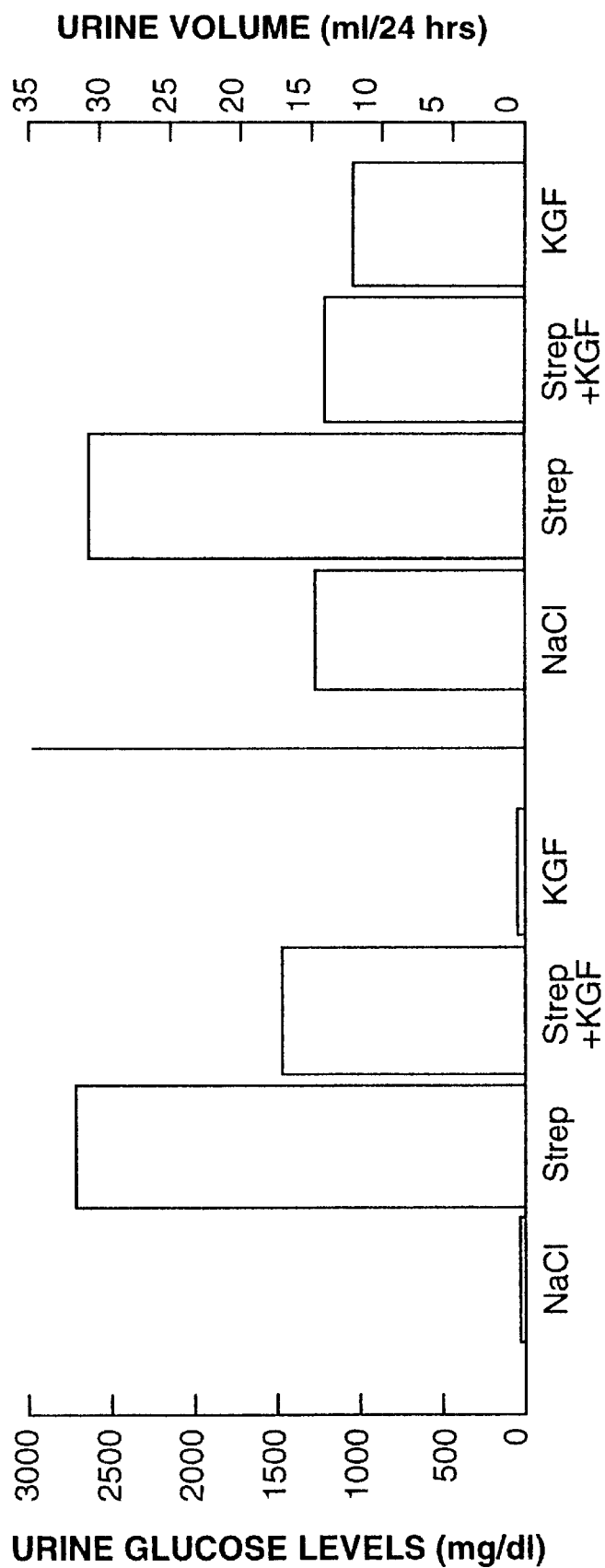

The non-fasting blood glucose level on the fifth day after administration of streptozotocin was significantly elevated in the diabetic control rats (group 2) in comparison with the non-diabetic control rats (group 1), as seen in FIG. 1. Diabetic rats which had been pretreated with KGF before streptozotocin administration and post-treated with KGF (group 3) had a significantly lower non-fasting blood glucose level than non-KGF treated diabetic controls (group 2), but still elevated relative to the non-diabetic control (group 1); see FIG. 1. The fasting urine glucose level and urine volume of the group 2 diabetic control rats were significantly elevated on the seventh day of the study (i.e., five days after injection with streptozotocin), as seen in FIG. 2. This condition is due to the destruction of the insulin-producing beta-cells in the pancreatic islets and the severe dysregulation of glucose metabolism which results in excretion of glucose in the urine. In contrast to this, the diabetic rats of (group 3, which were pre- and post-treated with KGF, showed significantly less elevation in fasting urine glucose than the diabetic control (group 2). The urine output for the KGF-treated group was also significantly less than for the diabetic control group; see FIG. 2.

These results are consistent with the induction of a moderate state of diabetes in the rat using streptozotocin as the inducing agent. Those diabetic rats which were treated with KGF prior to diabetes induction, and for which KGF was also continued after the induction, showed symptoms indicative of a milder form of diabetes. Thus, it can be concluded that the KGF therapy either partially prevented induction of the disease or restored insulin-producing islet cells after streptozotocin-induced beta cell destruction. In order to distinguish between these possibilities, KGF therapy beginning after disease induction was next studied.

Second Study: Using the same diabetes model previously described, the effectiveness of KGF to treat diabetes was further evaluated utilizing the following three groups of test rats:

1. Control rats treated with subcutaneously administered sodium chloride solution, no streptozotocin;
2. Rats made diabetic with intravenously administered streptozotocin, and post-treated with subcutaneously administered sodium chloride solution; and
3. Rats made diabetic with intravenously administered streptozotocin, then post-treated with subcutaneously administered C(1,15)S.

Figure 3:
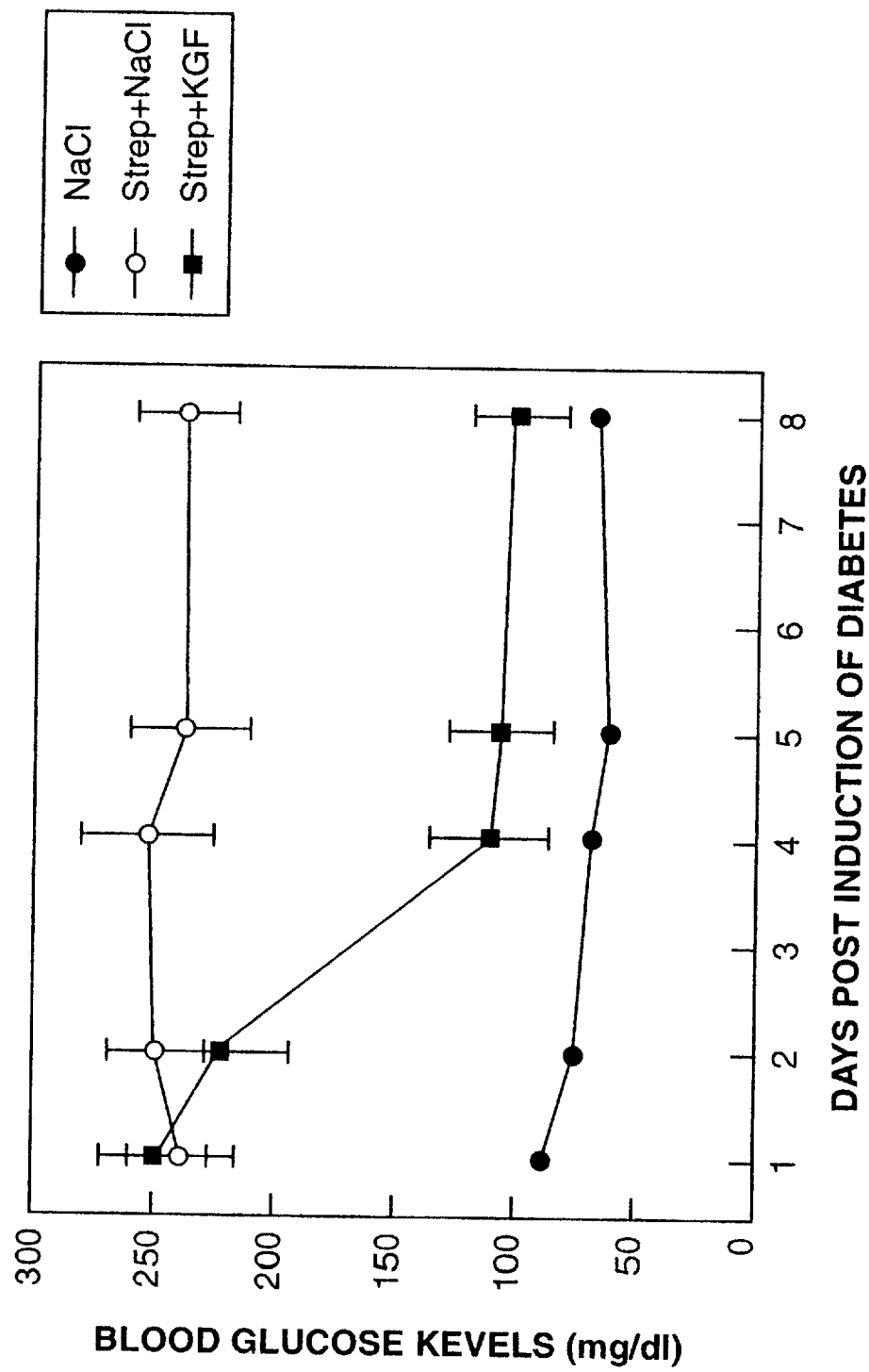
Figure 4:
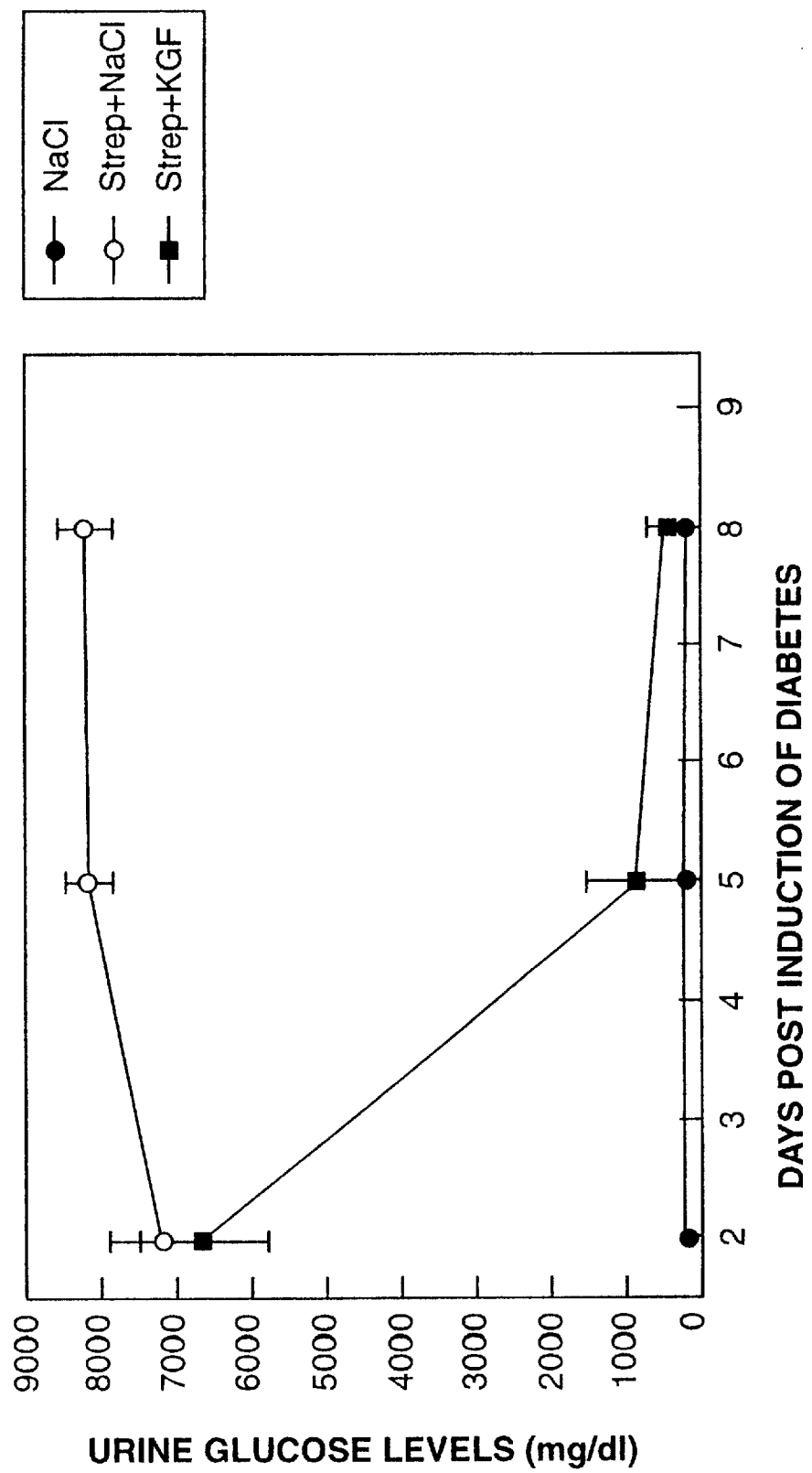
Figure 5:
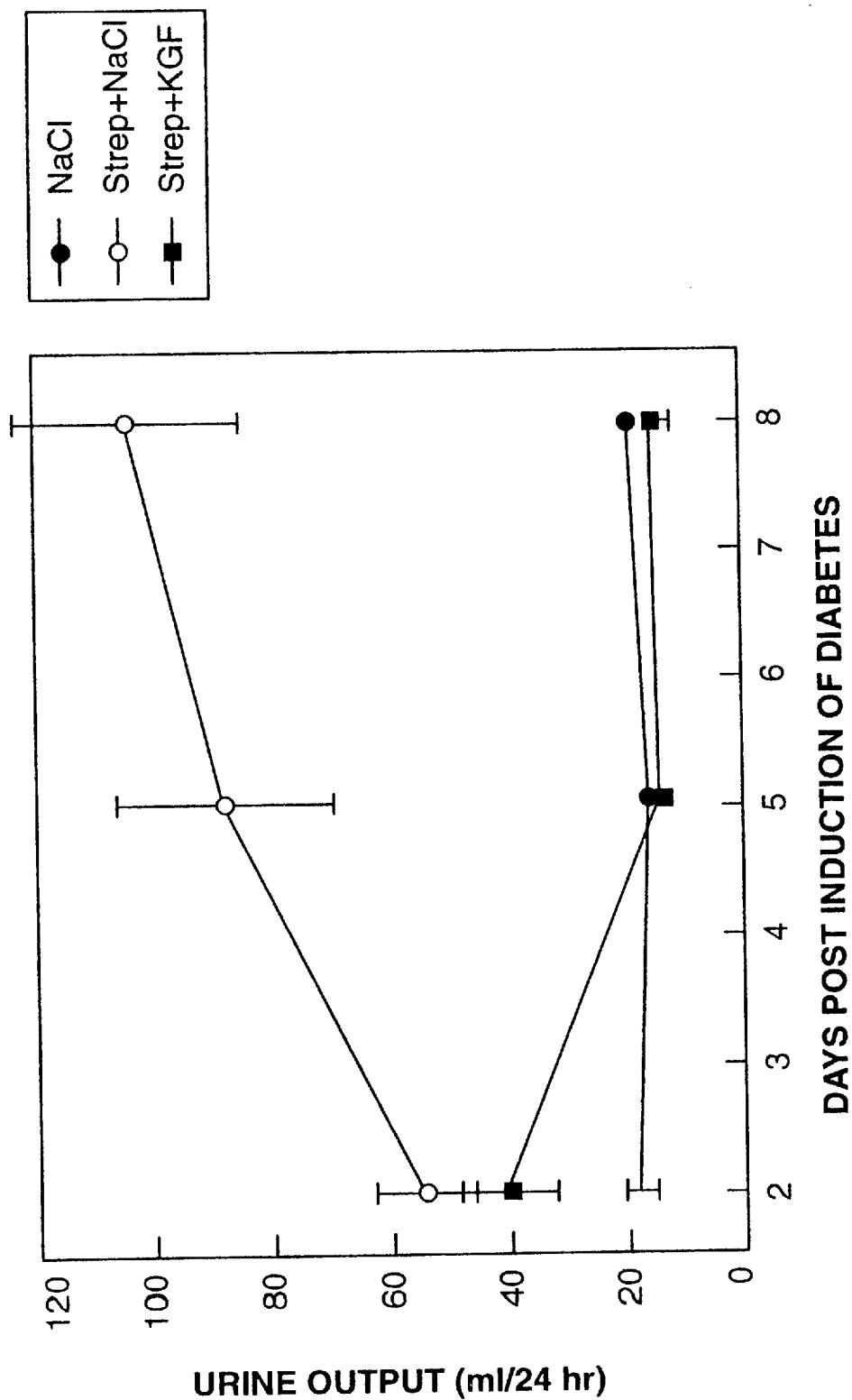
Figure 6:
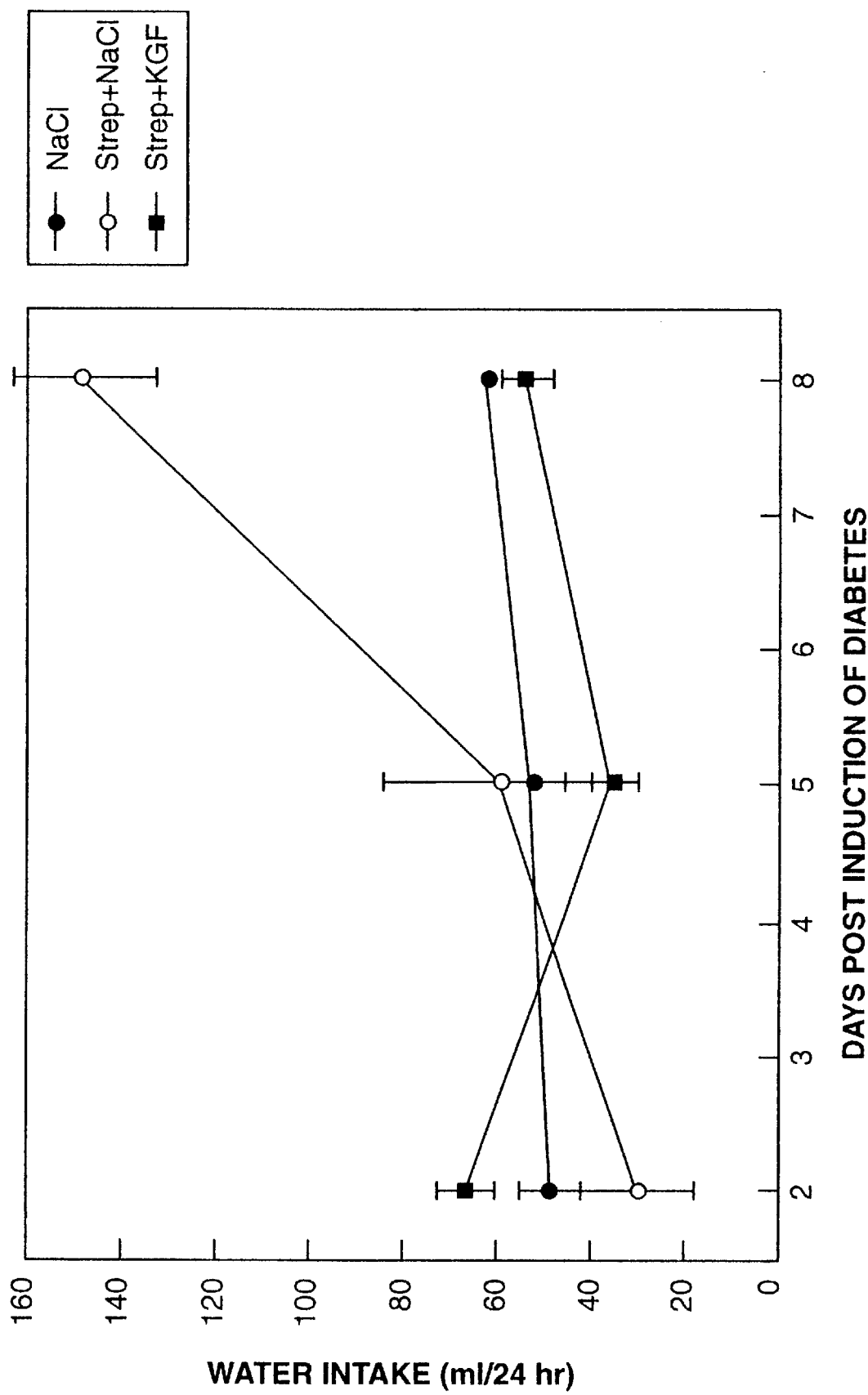

Test rats were administered at a dose of 3 mg/kg per day or sodium chloride solution over a period of thirteen days beginning one day after diabetes induction. The blood glucose level, urine glucose level, volume of urine output and water imbibed each under fasting and non-fasting conditions were monitored throughout the test period. The rats became diabetic in groups 2 and 3 within a day of administration of streptozotocin (FIG. 3). KGF therapy began in group 3 at twenty four hours after streptozotocin and was continued daily thereafter. Non-fasting blood glucose was measured on days 1,2,4,5 and 8. As FIG. 3 demonstrates, KGF therapy in group 3 was able to decrease the circulating blood glucose level to near that of control rats (group 1) by day 4, and this continued through day 8. The non-fasting urinary excretion of glucose was also measured on days 2,5 and 8. FIG. 4 demonstrates that KGF therapy decreased urinary glucose levels over 8-fold. Similarly, urine output in the KGF-treated diabetic rats was also normalized when measured on day 5 and day 8 (FIG. 5). Water intake, in milliliters per twenty-four hour period, did not increase in the KGF-treated diabetic rats as it did in the diabetic rats receiving sodium chloride solution as a control (FIG. 6). The rats were fasted overnight on day 8 and fasting blood glucose levels on day 9 were not different between these three groups. Fasting water intake and urine output were significantly less in the KGF-treated diabetic rats when compared to diabetic rats on day 9, which is further indicative of amelioration of the disease condition.

Third Study: The third study was a repeat of the second study and confirmed the data presented in FIGS. 3–6. Additionally, in this experiment, when the rats were necropsied the entire pancreas was removed from each rat and the insulin and C-peptide was extracted and quantitated. Table 1, below, shows the average amount of insulin or C-peptide extractable from the pancreas in each of the three groups. KGF therapy was able to increase the total content of insulin and C-peptide in the pancreas of diabetic rats when compared to diabetic rats treated with sodium chloride solution.

TABLE 1

| Total Pancreatic Content of: | | |
|---|---|---|
| Group[1] | Insulin (μg) | C-Peptide (μmole) |
| Control | 83.7 ± 6.7[2] | 3.5 ± 0.1 |
| Diabetic plus NaCl therapy | 6.4 ± 3.3 | 0.4 ± 0.1 |
| Diabetic plus KGF therapy | 18.9 ± 7.4 | 1.0 ± 0.3 |

[1]n = 3 – 4 rats per group
[2]Average ±S.E.

Figure 7:
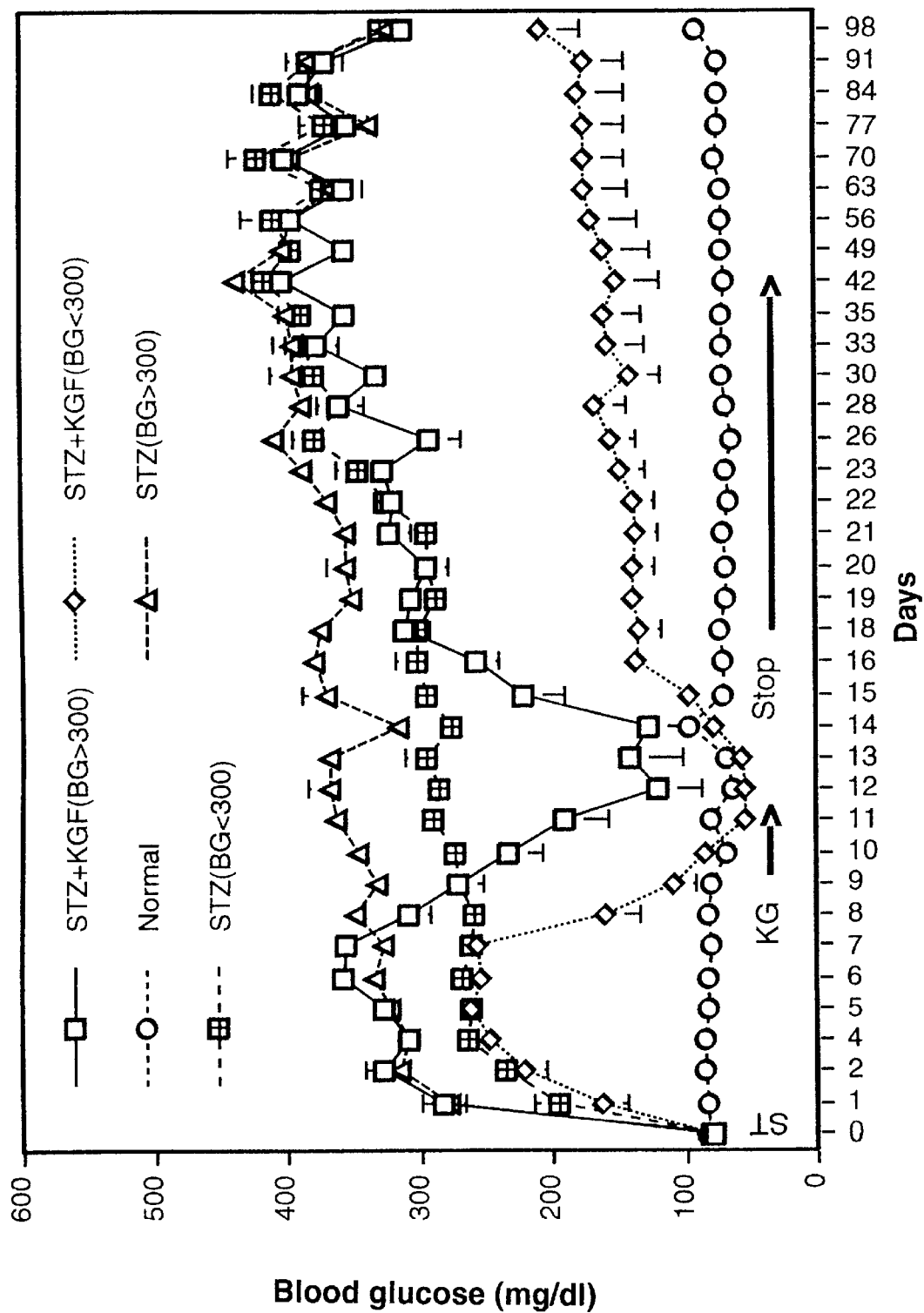
FIG. 7 shows the effect of a KGF analog on streptozotocin-induced diabetes in Sprague-Dawley rats.

The fourth study investigated the effect of KGF on streptozotocin-induced diabetes in Sprague-Dawley rats. On day 0, groups of rats were exposed to either 45 or 50 mg/kg streptozotocin (STZ). Following these treatments, non-fasting blood glucose levels were monitored daily to assess the severity of the islet injury. On day 5, the STZ-treated animals were placed into one of two groups (20/group) depending on the magnitude of hyperglycemia. The dividing point was set at a blood glucose level of 300 mg/dl. A group of non STZ-treated animals served as controls. On day 7, 10 animals from each hyperglycemic group were given ΔN23 (3 mg/kg/day) or PBS by subcutaneous injection for 7 days. Blood glucose levels were then monitored daily, every other day, or weekly and are set forth in FIG. 7. Note that STZ-treated animals from both groups receiving KGF had significant declines in blood glucose during the KGF dosing period. Importantly, the mean blood glucose drop experienced by the STZ-treated animals from the <300 mg/dl starting blood glucose group stabilized at about 150 mg/dl whereas the blood glucose drop seen in the >300 mg/dl starting blood glucose group was only transient. Note that the day scale is non-linear.

---

What is claimed is:

1. A method of treating diabetes mellitus, comprising administering to a mammal having that condition an amount effective for reducing blood glucose levels compared to an untreated individual of a keratinocyte growth factor having amino acid residues 32–194 of SEQ ID NO:2 (native KGF) or an analog thereof which comprises a difference from the sequence of native KGF by having an amino acid deletion of or having a residue other than cysteine substituted for $Cys^{32}$ and $Cys^{46}$ of SEQ ID-NO:2, wherein said keratinocyte growth factor exhibits at least 500-fold greater stimulation of BALB/MK keratinocyte cells than that of NIH/3T3 fibroblast cells and at least about 500-fold greater stimulation of BALB/MK keratinocyte cells than for BS/589 epithelial cells or for CC1208 epithelial cells, as determined by H-thymidine incorporation.

2. The method according to claim 1, wherein the keratinocyte growth factor is methionylated or nonmethionylated, native KGF, C(1,15)S, ΔN15–ΔN24, ΔN3/C(15)S, ΔN3/C(15)-, ΔN8/C(15)S, ΔN8/C(15)-, C(1,15)S/R(144)E, C(1,15) S/R(144)Q, ΔN23/R(144)Q, C(1,15,40)S, C(1,15,102)S, C(1,15,102,106)S, ΔN23/N(137)E, ΔN23/K(139)E, ΔN23/K(139)Q, ΔN23/R(144)A, ΔN23/R(144)E, ΔN23/R(144)L, ΔN23/K(147)E, ΔN23/K (147)Q, ΔN23/K(153)E, ΔN23/K(153)Q and ΔN23/Q(152)E/K(153)E.

3. The method according to any one of claims 1 or 2, wherein the keratinocyte growth factor is produced in bacterial cells.

4. The method according to claim 3, wherein the keratinocyte growth factor is produced in *E. coli*.

5. The method according to any one of claims 1 or 2, wherein the keratinocyte growth factor is formulated with a pharmaceutically acceptable carrier.

6. The method according to claim 5, wherein the pharmaceutically acceptable carrier is a long-term, slow release formulation.

7. The method according to any one of claims 1 or 2, wherein the keratinocyte growth factor is administered by parenteral injection.

8. The method according to claim 7, wherein the keratinocyte growth factor is administered in an amount from about 0.001 milligrams to about 10 milligrams per kilogram of body weight per day.

9. The method according to claim 8, wherein the amount of keratinocyte growth factor is from about 0.05 milligrams to about 5 milligrams per kilogram per day.

10. The method according to claim 7, wherein the mammal is a human.

11. The method of claim 7 wherein the parenteral injection is selected from the group consisting of subcutaneous, intravenous and intramuscular injection.

\* \* \* \* \*

SEQUENCE LISTING

```
<160>  2

<210>  1

<211>  862

<212>  DNA

<213>  Human

<220>

<221>  CDS

<222>  (108)..(689)

<400>  1 caatctacaa    ttcacagata    ggaagaggtc    aatgacctag    gagtaacaat    caactcaaga    60
ttcattttca    ttatgttatt    catgaacacc    cggagcacta    cactata   atg   cac   aaa        116
                                                                  Met   His   Lys
                                                                   1 tgg   ata   ctg   aca   tgg   atc   ctg   cca   act   ttg   ctc   tac   aga   tca   tgc   ttt   164
Trp   Ile   Leu   Thr   Trp   Ile   Leu   Pro   Thr   Leu   Leu   Tyr   Arg   Ser   Cys   Phe
      5                             10                            15 cac   att   atc   tgt   cta   gtg   ggt   act   ata   tct   tta   gct   tgc   aat   gac   atg   212
His   Ile   Ile   Cys   Leu   Val   Gly   Thr   Ile   Ser   Leu   Ala   Cys   Asn   Asp   Met
20                            25                            30                            35 act   cca   gag   caa   atg   gct   aca   aat   gtg   aac   tgt   tcc   agc   cct   gag   cga   260
Thr   Pro   Glu   Gln   Met   Ala   Thr   Asn   Val   Asn   Cys   Ser   Ser   Pro   Glu   Arg
                         40                            45                            50 cac   aca   aga   agt   tat   gat   tac   atg   gaa   gga   ggg   gat   ata   aga   gtg   aga   308
His   Thr   Arg   Ser   Tyr   Asp   Tyr   Met   Glu   Gly   Gly   Asp   Ile   Arg   Val   Arg
                  55                            60                            65 aga   ctc   ttc   tgt   cga   aca   cag   tgg   tac   ctg   agg   atc   gat   aaa   aga   ggc   356
Arg   Leu   Phe   Cys   Arg   Thr   Gln   Trp   Tyr   Leu   Arg   Ile   Asp   Lys   Arg   Gly
            70                            75                            80 aaa   gta   aaa   ggg   acc   caa   gag   atg   aag   aat   aat   tac   aat   atc   atg   gaa   404
Lys   Val   Lys   Gly   Thr   Gln   Glu   Met   Lys   Asn   Asn   Tyr   Asn   Ile   Met   Glu
      85                            90                            95 atc   agg   aca   gtg   gca   gtt   gga   att   gtg   gca   atc   aaa   ggg   gtg   gaa   agt   452
Ile   Arg   Thr   Val   Ala   Val   Gly   Ile   Val   Ala   Ile   Lys   Gly   Val   Glu   Ser
```

```
                100                      105                     110                     115
gaa   ttc   tat   ctt   gca   atg   aac   aag   gaa   gga   aaa   ctc   tat   gca   aag   aaa        500
Glu   Phe   Tyr   Leu   Ala   Met   Asn   Lys   Glu   Gly   Lys   Leu   Tyr   Ala   Lys   Lys
            120                         125                         130 gaa   tgc   aat   gaa   gat   tgt   aac   ttc   aaa   gaa   cta   att   ctg   gaa   aac   cat        548
Glu   Cys   Asn   Glu   Asp   Cys   Asn   Phe   Lys   Glu   Leu   Ile   Leu   Glu   Asn   His
                  135                         140                               145 tac   aac   aca   tat   gca   tca   gct   aaa   tgg   aca   cac   aac   gga   ggg   gaa   atg        596
Tyr   Asn   Thr   Tyr   Ala   Ser   Ala   Lys   Trp   Thr   His   Asn   Gly   Gly   Glu   Met
            150                         155                         160 ttt   gtt   gcc   tta   aat   caa   aag   ggg   att   cct   gta   aga   gga   aaa   aaa   acg        644
Phe   Val   Ala   Leu   Asn   Gln   Lys   Gly   Ile   Pro   Val   Arg   Gly   Lys   Lys   Thr
      165                         170                         175 aag   aaa   gaa   caa   aaa   aca   gcc   cac   ttt   ctt   cct   atg   gca   ata   act             689
Lys   Lys   Glu   Gln   Lys   Thr   Ala   His   Phe   Leu   Pro   Met   Ala   Ile   Thr
180                         185                         190 taattgcata   tggtatataa   agaacccagt   tccagcaggg   agatttcttt   aagtggactg                          749
ttttctttct   tctcaaaatt   ttctttcctt   ttatttttta   gtaatcaaga   aaggctggaa                          809
aaactactga   aaaactgatc   aagctggact   tgtgcattta   tgtttgtttt   aag                                 862
```

<210> 2

<211> 194

<212> PRT

<213> Human

<400> 2

```
Met   His   Lys   Trp   Ile   Leu   Thr   Trp   Ile   Leu   Pro   Thr   Leu   Leu   Tyr   Arg
  1                     5                        10                              15

Ser   Cys   Phe   His   Ile   Ile   Cys   Leu   Val   Gly   Thr   Ile   Ser   Leu   Ala   Cys
                  20                        25                        30

Asn   Asp   Met   Thr   Pro   Glu   Gln   Met   Ala   Thr   Asn   Val   Asn   Cys   Ser   Ser
                  35                        40                        45

Pro   Glu   Arg   His   Thr   Arg   Ser   Tyr   Asp   Tyr   Met   Glu   Gly   Gly   Asp   Ile
            50                        55                        60

Arg   Val   Arg   Arg   Leu   Phe   Cys   Arg   Thr   Gln   Trp   Tyr   Leu   Arg   Ile   Asp
 65                           70                        75                              80

Lys   Arg   Gly   Lys   Val   Lys   Gly   Thr   Gln   Glu   Met   Lys   Asn   Asn   Tyr   Asn
                        85                        90                        95

Ile   Met   Glu   Ile   Arg   Thr   Val   Ala   Val   Gly   Ile   Val   Ala   Ile   Lys   Gly
                  100                       105                       110

Val   Glu   Ser   Glu   Phe   Tyr   Leu   Ala   Met   Asn   Lys   Glu   Gly   Lys   Leu   Tyr
            115                       120                       125

Ala   Lys   Lys   Glu   Cys   Asn   Glu   Asp   Cys   Asn   Phe   Lys   Glu   Leu   Ile   Leu
      130                       135                       140

Glu   Asn   His   Tyr   Asn   Thr   Tyr   Ala   Ser   Ala   Lys   Trp   Thr   His   Asn   Gly
145                       150                       155                             160

Gly   Glu   Met   Phe   Val   Ala   Leu   Asn   Gln   Lys   Gly   Ile   Pro   Val   Arg   Gly
                  165                       170                             175

Lys   Lys   Thr   Lys   Lys   Glu   Gln   Lys   Thr   Ala   His   Phe   Leu   Pro   Met   Ala
                  180                       185                       190

Ile   Thr
```